United States Patent
Deagle

(10) Patent No.: US 6,730,667 B2
(45) Date of Patent: May 4, 2004

(54) IONTOPHORESIS DISC PAIN BLOCKER

(76) Inventor: William R. Deagle, 2755 S. Locust St., Suite 107, Denver, CO (US) 80222

( * ) Notice: Subject to any disclaimer, the term of this patent is extended or adjusted under 35 U.S.C. 154(b) by 222 days.

(21) Appl. No.: 09/995,117

(22) Filed: Nov. 26, 2001

(65) Prior Publication Data

US 2003/0100884 A1 May 29, 2003

(51) Int. Cl.[7] ............ A61K 31/55; A61K 31/205; A61K 31/165; A61K 9/14
(52) U.S. Cl. ............ 514/217; 514/555; 514/621; 424/484; 424/488
(58) Field of Search ............ 424/449, 443, 424/448, 484, 488; 514/217, 555, 621; 604/501

(56) References Cited

U.S. PATENT DOCUMENTS

| | | | |
|---|---|---|---|
| 5,795,909 A | * | 8/1998 | Shashoua et al. ............ 514/449 |
| 6,451,857 B1 | * | 9/2002 | Hurtt et al. ............ 514/561 |
| 6,572,880 B2 | * | 6/2003 | Murdock et al. ............ 424/449 |
| 6,576,636 B2 | * | 6/2003 | Webb et al. ............ 514/263.38 |
| 6,593,368 B2 | * | 7/2003 | Magnus-Miller et al. ... 514/561 |
| 6,602,902 B2 | * | 8/2003 | Shashoua et al. ............ 514/449 |
| 2003/0026850 A1 | * | 2/2003 | Bottaro et al. ............ 424/617 |

* cited by examiner

*Primary Examiner*—Vickie Kim
(74) *Attorney, Agent, or Firm*—Kyle W. Rost

(57) ABSTRACT

Treatment of pain syndromes utilizes a topical polypharmaceutical preparation of phenoxybenzamine, ketamine, gabapentin, nifedipine, carbamazepine, or combinations of them. Other suitable components are blockers of sympathetic alpha 1, 2 and other receptors, NMDA receptor blockers, GABA receptor blockers, AMPA receptor blockers, nitric oxide synthase receptor blockers, calcium channel blockers, ACDP receptor blockers, prostaglandin and leukotriene blockers, substance P blockers, bradykinin and neurotenin as well as other peptide blockers, and TNF alpha blockers. Recommended delivery is by locating a predetermined neurodermal point and locating a gel patch over the predetermined neurodermal point. Iontophoresis then delivers the pharmaceutical agent from the gel patch.

8 Claims, 2 Drawing Sheets

IONTOPHORESIS DISC PAIN BLOCKER

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The invention generally relates to surgery and to a method and means for introducing or removing material from the body for therapeutic purpose. More specifically, the invention relates to apparatus and method in which electrical energy is applied to the body, such as by iontophoresis. Similarly, the invention may have application in a method and apparatus for surgery in which material is introduced into or removed from a body orifice or inserted or removed subcutaneously other than by diffusing through skin. The invention has application to a method of enhanced absorption of therapeutic material using iontophoretic treatment. A specific focus is blocking pain by precision administration of suitable treatment.

2. Description of Related Art Including Information Disclosed Under 37 CFR 1.97 and 1.98

Treatment of pain in humans is a topic of increasing research emphasis. One promising approach is by use of topical cocktails of ingredients for blocking pain from many origins. Rather than offering mere additive results, the multi-component cocktail of ingredients promises an unexpectedly high level of efficacy. Another developing approach is the use of improved delivery systems, which often can be used for the administration of treatments for diseases and conditions not solely limited to pain. Such delivery systems employ, gels creams, ointments, patches, bioadhesives, and iontophoresis that can deliver a variety of pharmaceuticals, alone or in combined administration. These approaches are exemplified in the following patents.

U.S. Pat. No. 5,900,249 to Smith discloses treatment of specific types and causes of pain by administration of a multi-component topical composition. For example, one component offers anesthetic pain relief that masks pain but does not correct the underlying cause. Another component reduces the sensation of pain by alleviating the physiological and neurotransmitter etiology of the pain. Each of the various active components functions differently in order to treat pain comprehensively, regardless of causes. Multiple components include, first, a vasodilating agent such as nifedipine; second, an antiinflammatory agent to reduce pain mediated by prostaglandins; third, a membrane stabilizing agent such as carbamazepine; and fourth, seratogenic and nonadrenergic reuptake inhibitor. These may be supplemented with a topical anesthetic and an anti-inflammatory steroid. These medications are delivered in a gel, ointment, or cream.

U.S. Pat. No. 5,837,289 to Grasela discloses a general purpose delivery system that employs transdermal delivery of medication in a patch. Iontophoresis is useful with the medication in the patch to increase skin permeation. A topical delivery system may use a cream carrying the desired medication plus penetration enhancers.

U.S. Pat. No. 6,210,394 Demopulos discloses a cocktail of pain blocking agents for topical administration by irrigating with combined inhibitors for both pain and inflammation. The treatment addresses pain caused by multiple distinct sources of pain, including prostaglandin, bradykinin, histamine, and serotonin. Each source can be inhibited by application of the corresponding receptor antagonists. The cocktail of anti-pain/anti-inflammation agents can be composed of fourteen classes of receptor antagonists and agonists, plus optional anti-spasm agents. An aspect of the treatment is a resulting synergy in certain combinations, believed to result from cross talk between various signaling pathways.

The practice of iontophoresis is useful to deliver a drug to a subject by driving charged ions of the drug through the skin of the subject by applying an electric potential. The effective component of the drug must carry a charge, and the electrical apparatus must be polarized in the proper direction to deliver the charged component. For example, a patch containing a drug with positive charge is applied to the skin of a subject. The patch is connected to the iontophoretic delivery system at the positive electrode. A negative electrode is connected elsewhere to the subject to complete a closed pathway for the electric current.

A recent and representative discussion of iontophoresis appears in U.S. Pat. No. 6,235,013 to Tapper. An iontophoretic patch and administration system employ alternating current of low frequency in order to avoid problems of skin damage and pH imbalance during administration.

Electrical probes can detect numerous topical points in the skin that show a dramatic drop in skin resistance, as measured in meg ohms. These points are neurodermal points and are identified as Langerhans complexes. They have a pattern in dermis tissues much like a grid. The presence of these neurodermal points has been known for a long time. In ancient China, equivalent points were known as points of Chi or energy, and in India they were called Prahna. In fact, they are a normal complex of afferent and efferent A delta sensory myelinated nerves, small unmyelinated "C fibers," and tiny endocrine organelles. Such structures are capable of releasing NO, nitric oxide, and gamma amino butyric acid (GABA). They are also capable of locally releasing a variety of substances. These include $Ca^{++}$ ions via the NMDA, aminocyclopentane-1,3-dicarboxylate (ACPD) receptors; substance P peptide; alpha-amino-3-hydroxy-5 methyl-4-isoxazolepropionic acid (AMPA) receptors; and glutamate.

Persons born without Langerhans complexes in the superficial dermis cannot suffer pain. Thus, the pain process requires the projection of painful nociceptive afferents from superficial and deep structure onto the dermal grid of the Langerhans network. The afferent modulation at this level of preprocessing determines if there is painful perception at each dermatome with central projection of these neural holograms to ever-higher levels of modulation at the dorsal horn, substantia gelatinosa areas V to IX, rostrally to the thalamus and tectum of the midbrain and onto the cortical modulation. This process determines patterns of proprioceptive interpretation and, thus, muscle static and dynamic firing patterns. Spasm is modulated via red fiber tonic muscle fibers that cause spinal and joint subluxation, and further nociceptor stimulation via A delta afferent pain fibers and C fiber pain afferents. The earliest pattern on EMG is spectral imbalance in surface EMG with non-physiologic phase shifts in axial paraspinal muscle firing and increased greater than 400 Hz efferents to the spinal myotome or peripheral muscles.

A number of known electrical probes employ an electric current or resistance measurement to aid in administering drugs or performing a medical procedure. A representative example appears in U.S. Pat. No. 3,862,162 to Colyer, which combines a hypodermic needle with an electrical probe. The probe is useful to locate a nerve, which can be treated by injecting a selected medicament through the needle. U.S. Pat. No. 5,853,373 to Griffith et al. suggests the use of a similar needle and probe combination in order to locate a nerve for administration of anesthetic. U.S. Pat. No. 5,284,153 to Raymond et al. suggests using a nerve stimulator either to assist in administration of regional anesthesia or to guard against cutting specific nerves during surgery.

Thus, a technology is known for locating a nerve or neurodermal point by electrical detection, and this has aided in administering certain types of treatments or drugs. However, this technology has not been adapted to improve the efficiency or effectiveness iontophoresis. In particular, the method of this invention improves iontophoresis by first using a probe to locate a neurodermal point, and then placing a patch containing the drug over the located point, and driving the drug into the subject by applying an electrical current across the patch and the subject's skin at the located point. The effectiveness of the treatment is improved, while the required quantity of drug often is substantially decreased. With a lower quantity of the drug required to be administered for effective treatment, the patient benefits by reduction in side effects. This results in an improved overall efficiency and effectiveness of treatment.

Further improvements in treatment are possible by selecting and formulating a polypharmaceutical preparation for application by topical means, which may include iontophoresis. The placement of an iontophoretic patch on a preselected neurodermal point, located by use of a probe, further improves the treatment.

An improved polypharmaceutical preparation can be formulated by the suitable selection and combination of an array of drugs. The preferred candidates include ketamine, which topically blocks the NMDA $Ca^{++}$ channels. Gabapentin also is a glutamate antagonist. Carbamazepine is an AMPA ($Na^+$ channel) receptor blocker, as is gabapentin. The 10–11 epoxide is the active molecule that modulates C fiber afferents at the Langerhans complex. Carbamazepine blocks peripheral sympathetic nerve receptors via the voltage-dependent sodium channels, in the same manner as it blocks these receptors in the dorsal root ganglion (DRG). Clonidine is an alpha 2 blocker that similarly blocks the alpha 2 receptor. Phenoxybenzamine is an alpha 1 agonist. It has much more power to block dorsal ganglionic afferents that synapse with the interneurons of the wide range neurons of areas V to IX of the dorsal horn, before ascending up Lissauer's spinothalamic tract, carrying afferent painful stimuli to the thalamus. Nifedipine is useful for non-NMDA, voltage-sensitive calcium-channel blockade, which down regulates nitric oxide (NO) synthesis.

Pluronic lecithin organogel (PLO), topical vehicle allows the above pharmaceuticals to penetrate to the dermis and modulate up regulated activity in all these pathways that cause acute and chronic pain, modulation at the periphery.

There are three phases of rehabilitation: phase one—increased activity at the same pain level; phase two—decreased pain at the same activity level; and phase three stabilization—damping of the sine wave fluctuation status with less severe and frequent flare-ups in pain, spasm and deconditioning. Such topical pharmacotherapy has proven effective on numerous patients at accomplishing benefits at all three phases of rehabilitation. Static and dynamic spasm is reduced, and dynamic eccentric-concentric contraction is restored to proper in-phase 180-degree muscle firing for oppositional muscles across the paraspinal myotomes and peripheral muscles. Restoration of oxygenation, with prevention of vasoconstriction all improved tissue healing and reduced low oxygen tension dependant induction of fibroblast collagen III generation that with later remodeling will produce adhesions and neural entrapments. In other words, barriers to movement, vasoconstriction, and healing are removed via topical peripheral pharmacological blockade. The neural holographic image of the pain is blocked before it can be projected rostrally to the thalamus and cortex, with resultant muscle firing abnormalities, postural and dynamic changes and vasoconstrictive changes with subsequent deconditioning and development of atrophy.

There are estimated to be 50 million Americans with partial or total disability due to chronic pain. The world market is estimated to be about $7.7 billion for analgesics in US dollars. The American Pain Society estimates 45% of the population seeks medical help for persistent pain at some point. The cost to American workers and companies, including lost workdays and physician visits, is in excess of $100 billion per year in America, alone.

New scientific evaluation tools such as Quantitative Sensory Nerve Threshold Testing using the MediDx 7000 to map sensory nerve and sympathetic nervous function can add the dimension of quantitative assessment of the patient's neuropathologic improvement or deterioration. Diagnostic spinal ultrasound (DSU) also will demonstrate improvements or deteriorations with changes to perineural edema and myofascial edema up to six inches on either side of the spinal cord sagittal plane, as well as changes in posterior element facet arthropathy. Application of these technologies can verify the efficacy as not only altering the patient's reported pain and loss of function, but also the quantitative physiological parameters of improvement in A delta and C fiber physiology, as well as joint, muscle and soft tissue edema and inflammatory change.

Most pain has a strong neuropathic component. Current over-the-counter (OTC) preparations are not benign. Thus, safer approaches without systemic side effects are required. Delivery of these effective but toxic or sedating pharmaceuticals avoids systemic effects and is very useful, safer and gives an element of control and validation back to the sufferer. An effective topical preparation can significantly reduce reliance on OTC preparations and on more powerful, orally administered, centrally acting pharmacotherapies that carry with them significant risks and side effects. More rapid recovery and lower use of oral and injected drug therapies are obvious benefits, leading to more rapid reconditioning, and maintaining fitness for duty at work and fitness for recreation. Suppressing the image of pain in the peripheral Langerhans dermal complexes results in suppression of the primary pain image at its primary projection sites of the Langerhans complex network. Such a polymodal pharmcotherpeutic management plan will prove to be a key step in all forms of pain control in the 21st century.

It would be desirable to improve the efficiency of treatment using iontophoresis by locating effective treatment sites. In addition, it would be desirable to formulate and administer more effective treatments for pain syndromes, both by addressing multiple pathways of pain propagation and administering such treatment by improved methods.

To achieve the foregoing and other objects and in accordance with the purpose of the present invention, as embodied and broadly described herein, the method and apparatus of this invention may comprise the following.

BRIEF SUMMARY OF THE INVENTION

A general object of the invention is to provide a new and improved composition and method of treatment of pain, utilizing topical preparations.

Another object is to provide a composition and method of the type described which provides the desired therapeutic response through topical administration in the form of cream-gel preparation, spray or aerosol, and topical iontophoresis methodology patch.

The invention provides a composition and method of treatment for alleviating pain. A solution of pharmaceuticals including phenoxybenzamine, ketamine, gabapentin, nifedipine, and carbamazepine in PLO carrier or other suitable topical preparation vehicle is applied topically to the painful region of the skin.

The invention is derived from research and observations showing local anesthetic blockade at the Langerhans complex network map of a pain-projected distribution. The mechanisms for pain modulation in the dermis provide a new theory of pain gate and prespinal cord modulation that can block afferent pain perception and the attendant reflex spasm, vasoconstriction, and atrophic and deconditioning effects that can result from a projected neural holographic image.

According to the invention, a method of administering a pharmaceutical agent suited for iontophoretic delivery to a human or animal subject is performed by, first, performing a point locating step by locating on a subject to be treated a preselected neurodermal point for receiving the pharmaceutical agent. Second, a patch application step is performed by applying to the subject, over the preselected neurodermal point, an iontophoretic patch containing the pharmaceutical agent to be administered. Third, a delivery step is performed by applying an electrical potential across the iontophoretic patch and the subject and delivering the pharmaceutical drug from the patch to the subject at the neurodermal point by iontophoresis.

According to another aspect of the invention, a polypharmaceutical composition for treating chronic pain by producing a blockade of the initiation and propagation of the pain stimulus in the Langerhans and other neuroendocrine vascular structures of the superficial and deep dermis is composed of, in combination, at least two pharmaceutical agents selected from the group consisting of an NMDA receptor blocker, a GABA receptor blocker, an AMPA receptor blocker, a nitric oxide synthase receptor blocker, a calcium channel blocker, an ACDP receptor blocker, a prostaglandin blocker, a leukotriene blocker, a substance P blocker, a bradykinin blocker, a neurotenin blocker, a peptide blocker, a TNF alpha blocker, a sympathetic alpha 1 receptor blocker, a sympathetic alpha 2 receptor blocker, and a non-NMDA calcium-channel blocker.

According to still another aspect of the invention, a method of treating pain by producing a blockade of the initiation and propagation of the pain stimulus in the Langerhans and other neuroendocrine vascular structures of the superficial and deep dermis, is performed through an administration step by topically administering to a person in need of such treatment an effective dosage of a combination of at least two pharmaceutical agents selected from the group consisting of an NMDA receptor blocker, a GABA receptor blocker, an AMPA receptor blocker, a nitric oxide synthase receptor blocker, a calcium channel blocker, an ACDP receptor blocker, a prostaglandin blocker, a leukotriene blocker, a substance P blocker, a bradykinin blocker, a neurotenin blocker, a peptide blocker, a TNF alpha blocker, a sympathetic alpha 1 receptor blocker, a sympathetic alpha 2 receptor blocker, and a non-NMDA calcium-channel blocker.

According to a further aspect of the invention, a method of treating pain in a human or animal subject by administering a combination of preselected effective pharmaceutical agents in an suitable dosage to treat a subject in need thereof, is carried out by, first, performing a point locating step by locating a predetermined neurodermal point associated with the pain. Second, the preselected pharmaceutical agents for treating pain are provided in a gel patch suited for delivery by electrically driving charged ions of the pharmaceutical agents from the path and into the subject. Third, an application step is performed by applying the provided gel patch to the predetermined neurodermal point on the subject. Fourth, a delivery step is performed by delivering the selected pharmaceutical agents from the patch to the subject by electrically driving charged ions of the pharmaceutical agents into the subject.

The accompanying drawings, which are incorporated in and forms a part of the specification illustrates preferred embodiments of the present invention, and together with the description, serves to explain the principles of the invention. In the drawings:

DETAILED DESCRIPTION OF THE INVENTION

Figure 1:
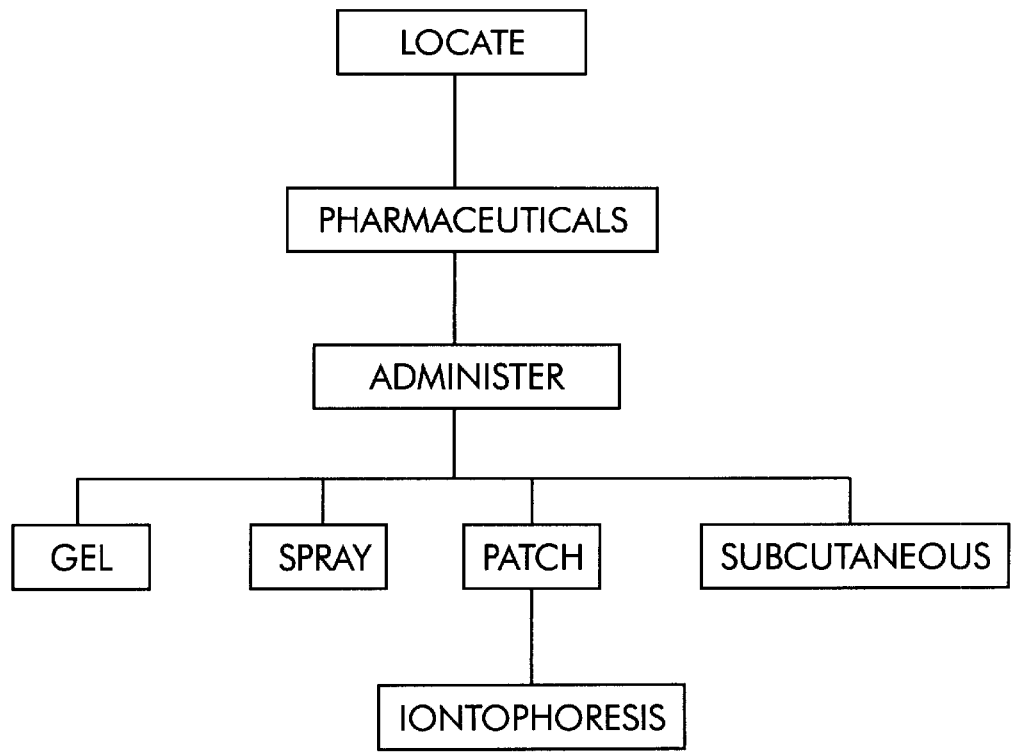
FIG. 1 is a schematic diagram of a method of delivering a pharmaceutical agent.

A first aspect of the invention is a method of administering a pharmaceutical drug suited for iontophoretic administration. According to the method, first locate a predetermined neurodermal point selected for its suitability for receiving the pharmaceutical drug. Second, apply an iontophoretic patch to the predetermined point. Third, apply an electrical potential across the patch and the subject to deliver the pharmaceutical drug to the subject by iontophoresis. Related aspects of this invention include the composition and structure of an iontophoretic disc or patch for use in the method.

A second aspect of the invention is a novel composition for treating chronic pain by producing a blockade of the initiation and propagation of the pain stimulus in the Langerhans and other neuroendocrine vascular structures of the superficial and deep dermis.

A third aspect of the invention is a method of treating pain by topically administering the novel composition of pharmaceutical agents, thereby producing a blockade of the initiation and propagation of the pain stimulus in the Langerhans and other neuroendocrine vascular structures of the superficial and deep dermis.

A fourth aspect of the invention is a method of administering the combination of pharmaceutical agents to treat pain, in which the composition is made available in an iontophoretic gel patch that is placed by locating a predetermined neurodermal point associated with the pain. The patch is applied to the predetermined neurodermal point. Iontophoresis delivers the pharmaceuticals by driving charged ions of effective agents into the patient.

When used in the treatment of pain, the compositions, methods, and apparatus of this invention will extinguish the neural hologram of the painful image, topically. The composition is comprised of pharmacologically acceptable salts of active compounds comprised of non-toxic acid addition salts and inorganic acids. Within the United States, "pharmacologically acceptable salts" preferably are those approved for use on humans by the United States Food and Drug Administration (FDA), to the extent such approval currently is required or may be required in the future. FDA approval is desirable in those geographic areas under the jurisdiction of the FDA for the treatment of humans, but it is not a limitation on the scope of the invention.

A unique composition and dosage form have been developed for the topical treatment of refractory neuropathic pain. The composition is a topical pharmaceutical composition for extinguishing the neural hologram of a painful image. The composition is a combination of ingredients that block various released agents that trigger the pain sensation. The released agents are NO (nitric oxide); GABA (gamma amino butyric acid); Ca++ ions via NMDA; ACPD (aminocyclopentane-1,3-dicarboxylate); substance P peptide; AMPA (alpha-amino-3-hydroxy-5 methyl-4-isoxazolepropionic acid); and glutamate. Broadly, the blocking agents target the following receptors: sympathetic alpha 1,2; NMDA; GABA; AMPA; nitric oxide synthase; calcium channel; ACPD; prostaglandin and leukotriene; substance P; bradykinin, neurotenin and peptide; and TNF alpha.

Selected components are combined and delivered in a topical vehicle, preferably pluronic lecithin organogel (PLO). Specific components are phenoxybenzamine; ketamine; gabapentin; nifedipine; carbamazepine; and clonidine. Methods of topical application are as cream, gel, ointment, spray or patch, especially by iontophoresis delivering the components through an iontophoretic patch.

A preferred composition consists of three selected active pharmaceutical agents: ketamine HCl USP, gabapentin, and phenoxybenzamine HCl. These three agents are incorporated into pluronic lecithin organogel (PLO) to facilitate transdermal administration.

The concentration by volume of the active pharmaceutical components are preferred to be approximately 2% phenoxbenzamine, 5% ketamine, and 5% gabapentin. The concentration of constituents in percent of solution may be varied for specific types of pain blockade, so as to obtain a desired therapeutic response for a particular patient population. These components are mixed in a controlled environment. Precautionary measures should protect pharmaceutical workers from active ingredients that may become airborne or be topically absorbed. In the United States, OSHA complaint safety procedures should be followed.

The composition includes a pharmaceutically acceptable liquid carrier serving as a vehicle, including a biphasic complex of lecithin and organogel, for molecular egression across the epidermis to the superficial and deep dermis where neuroendocrine vascular structures such as the Langerhans bodies reside. PLO is a phospholipid liposomal micro emulsion used for transdermal drug administration. It has two phases:

(1) Oil Phase: The oil phase is lecithin/isopropyl palmitate solution. Lecithin rearranges the horny layer of the skin. Isopropyl palmitate is a solvent and penetration enhancer. Sorbic acid is a preservative.

(2) Water Phase: The water phase is the pluronic gel. Pluronic f127 NF is a commercial surfactant. Potassium sorbate NF is a preservative. Purified water is a solvent. The active agents are incorporated into the PLO gel and a stable emulsion is formed through sheer force. The concentration of the active agents in the formulation may be adjusted as to obtain the optimal therapeutic response.

A composition of the active agents and carrier is prepared according to the following procedure. First, triturate the ketamine HCl USP, gabapentin, and phenoxybenzamine HCl, together using geometric dilution. Second, solubilize the chemical in purified water, USP. Third, combine the solubilized chemical with the lecithin/isopropyl palmitate solution and mix well. Fourth, add pluronic F127 20% gel in small increments to bring to desired volume. Fifth, mix at high rate of speed in electronic mortar and pestle to form smooth creamy gel.

Once prepared, the solution of pharmaceutical can be administered topically to the region of pain either by the patient or by a heath care provider. The form of dosage for topical administration includes solutions, suspensions or emulsions of the active components in a liquid carrier in the form of cream, gel, ointment, and topical iontophoresis methodology patch technology. Suitable carriers include pluronic lecithin organogel (PLO) or other suitable suspensions or carriers. When the dosage form is a topical cream-gel suspension or topical patch methodology, it may contain preservatives, stabilizers, emulsifiers or suspending agents, wetting agents, salts for osmotic pressure or buffers, as required. When the dosage form is as a pressurized spray or aerosol, the solution is contained in a pressurized container with a liquid propellant such as dichlorodifluroro methane or chlorotrifluoro ethylene. If administered from a pump container, the solution will include a buffer salt solution with preservatives, stabilizers, emulsifiers or suspending agents, wetting agents, and salts for osmotic pressure or buffers, as required.

When the composition is administered in the form of topical gel-cream, spray, or topical iontophoresis gel patch, the time of repeat application will vary from every six to twelve hours for the gel-cream and spray to several days for the topical iontophoresis gel-patch delivery methods. Occlusion with a barrier ointment or physical barrier such as hypoallergenic membrane may also be administered after topical application of the gel-cream or spray to increase efficacy and penetration of the pharmaceutical to active pharmaceutical sites in the dermis.

The following examples show the efficacy of the composition in treating chronic pain.

EXAMPLE I

A 44-year old female had a history of neck and upper back injury, with secondary chronic regional pain syndrome (CRPS), with continuous symptoms for 24 months post trauma, especially with activity and movement. The patient was treated with the topical polypharmaceutical preparation in PLO, and noted an immediate reduction in pain, increased movement with reduced activity induced pain and reduced referred pain and numbness into her upper extremities. Repeated use of the preparation resulted in continued accumulative reduction in pain and improved range of motion of the neck, upper back and upper extremities, and a significant reduction in a hypersensitivity of the skin to even light touch, which had been noted prior to treatment. The patient was maintained on the topical blockade on a permanent basis.

EXAMPLE II

A 49-year old male had a motor vehicle accident, with two level bulging cervical discs, and musculoligamentous instability at multiple levels in his cervical spine with pain twelve months following deceleration injury. Utilizing topical application of the preparation two to three times per day, he achieved a significant reduction in pain immediately, with improved range of motion. Accumulative benefit in further reduction of pain, improved range of motion and reduction of topical hypersensitivity to touch and activity were noted, with continued use. He was continued on the preparation on a permanent basis, during the rehabilitation and contributed greatly to his achieving higher spinal muscular tone and dynamic motor control, and less interference with activities of daily living (ADLs).

EXAMPLE III

A mid-twenties female patient with a lifting injury, resulting in bulging lumbar disc, myofascitis, and perineural as well as facet arthropathy identified on diagnostic spinal ultrasound (DSU) and MediDx 7000 quantitative sensory nerve conduction threshold testing, was treated with the topical preparation. She noted immediate reduction in pain with application and accumulative pain reduction, with improved lower extremity temperature, reduction in muscle spasms, and improved spinal postural and dynamic motor control. Accumulative improvements were noted in all the above areas. She was continued on the topical preparation during the entire period of her rehabilitation, and it contributed greatly to reduction in barriers to reconditioning, and maintaining increased activity levels, with reduction in problems with ADLs.

FIG. 1 illustrates an overview of the method practiced in this invention 10. The preferred methodology 10 for administering the treatment is to perform a locating step 12 to identify neural points. For this purpose, a suitable instrument is an electronic point finder that has the capability to identify nerves or neural points, which can be detected by their relatively lower electrical resistance compared to surrounding body or skin areas. U.S. Pat. No. 5,284,153 to Raymond discloses one such point finder and is incorporated by reference herein for disclosure of such devices. A variety of such instruments are commercially available and often combine functions of selectively detecting a nerve and selectively applying an electrical current to stimulate the nerve.

Once the desired nerve or nerves are identified, a preselected composition of pharmaceuticals 14 is prepared for an administration step 16. Administration may be topical, by methods including gel 18 or spray 20. Iontophoresis is a preferred method. The composition is applied to a patch 22 for iontophoretic administration. Suitable patch structures include both single and multi-layered gel matrix discs. For example, a patch may be arranged with one or more layers of pH buffered electrolytes between drug layers. Ionotphoresis 24 delivers the drugs by application of tiny unipolar or switchable bipolar micro amperage current to the gel disc over the next 24 to 36 plus hours, producing blockade to the excessive nerve firing.

As a result of practical patient experience, two components have been found to work well for delivery by iontophoresis. These are ketamine, which is an NMDA receptor blocker, at 2 to 4% or higher, and clonidine, which is an alpha 1 sympathetic receptor blocker, at 0.2 to 0.4% concentration, unbuffered. Both have positive polarity, and are positive charged. Selection of positive polarity would push the drug along the pathway of least resistance, finding the involved overactive nerve fibers; and pain blockade would occur.

Several different methods or devices can perform iontophoretic administration. The composition can be administered by use of a known personal iontophoretic device. Alternatively, a treatment disc can be preloaded with gel layers of this or other listed and potential pharmaceuticals. The treatment disc 50 of FIG. 2 includes a wafer micro battery 56 for applying an electrical potential through the gel layers and across the skin of the patient. Such a treatment disc would release the pharmaceuticals over the identified skin surface and into the previously identified nerves that are causing the local pain response and contributing to the level one skin-spinal nerve root-paraspinal ganglionic pain hologram.

A variety of point finders are known and may be used to identify the nerve to be targeted. Two types of point finders are commercially available and are preferred choices.

Type 1—Acupuncture Point Finder:

This type of point finder measures electrical resistance by applying a small test current between positive and negative electrodes, which typically are in close proximity to each other on the tip of a probe. A light or sound indicates when a nerve or other pathway of reduced skin resistance has been found. Some of these devices, such as those produced by Siemens Scientific, can identify the drop of skin resistance in mega ohms.

Type 2—Motor Stimulation Nerve Finder:

This type of point finder is a nerve stimulator. A surface electrode is applied along the skin to identify a current path, and an electrical signal is applied to produce a muscle response. Several typical types of signals are used. These are known as a 50 to 100 Hz tentanic stimulus, a DBL burst, a Train-Of-Four stimulus, or a Twitch stimulus. These same types of signals are commonly used in pain facilities to identify nerves before selective nerve root blocks, after producing a muscle response along the neurovascular bundle.

Figure 2:
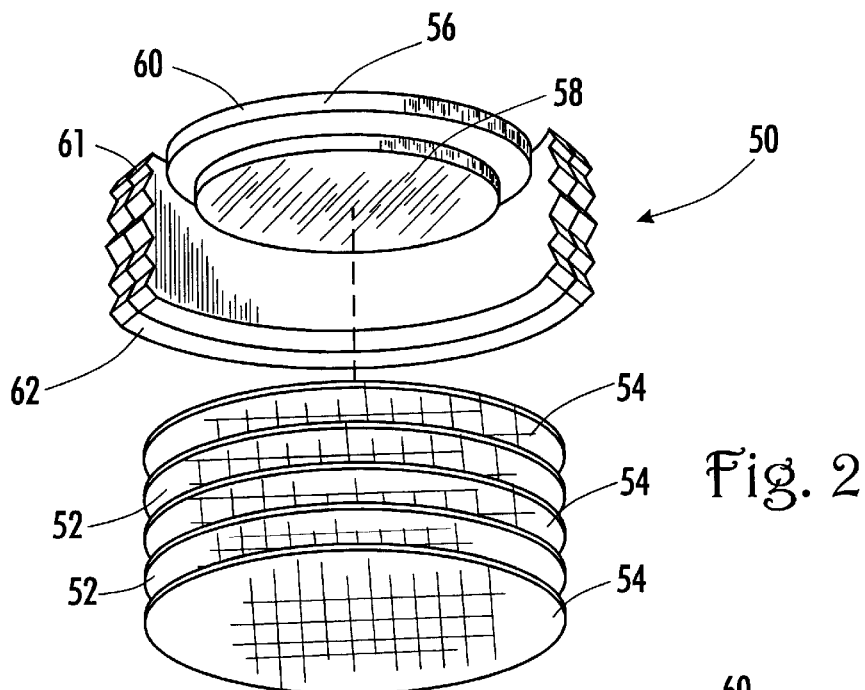
FIG. 2 is an isometric assembly view of a multi-layer iontophoretic patch disc with a wafer battery and layers of pharmaceutical gel and buffers, showing the side and bottom portions of the disc, and with portions of a contact ring and dielectric ring broken away for clarity.

A gel disc as shown in FIG. 2 may be prepared for the iontophoresis pain blockade. The disc 50 includes a patch composed of a multilayer structure in which each of the three pharmaceutical agents is in a separate layer 54. Each layer of an active agent is separated from any other layer of active agents by an interposed layer of electrolyte buffered gel 52.

In order to deliver the composition to a patient using electrical assistance, the gel disc is connected to a current source such as a battery 56. A first pole of the current source may contact the gel patch, and a second pole may contact the skin of a patient. For example, in the view of FIG. 2, the first pole 58 may be the lower face of the disc battery. This battery contact face 58 is positioned in electrical contact with an outer face or top of the gel disc so that current can flow through the patch between the battery and the patient's skin. The opposite or second pole 60 of the current source may be the upper face of the disc battery. This battery contact face 60 is positioned in electrical contact with a peripheral portion of the disc, such as ring 62 that is in electrical contact with the skin of the patient when the patch is used. The two poles are in a closed circuit formed when the disc is applied to the patient's skin.

A peripheral ring 62 is the preferred configuration of the skin-contacting portion of pole 60. However, regardless of its shape, the contact 62 should be located at an offset position from the gel patch so that current flows through the patient's skin in order to complete the circuit. A concentric dielectric insulating ring 64 lies within the contact ring 62. It insulates both the wafer battery 56 and the gel disc 52,54 from the second pole of the battery. This insulator ensures that the two poles of the battery cannot form a closed circuit without an external current pathway.

Figure 3:
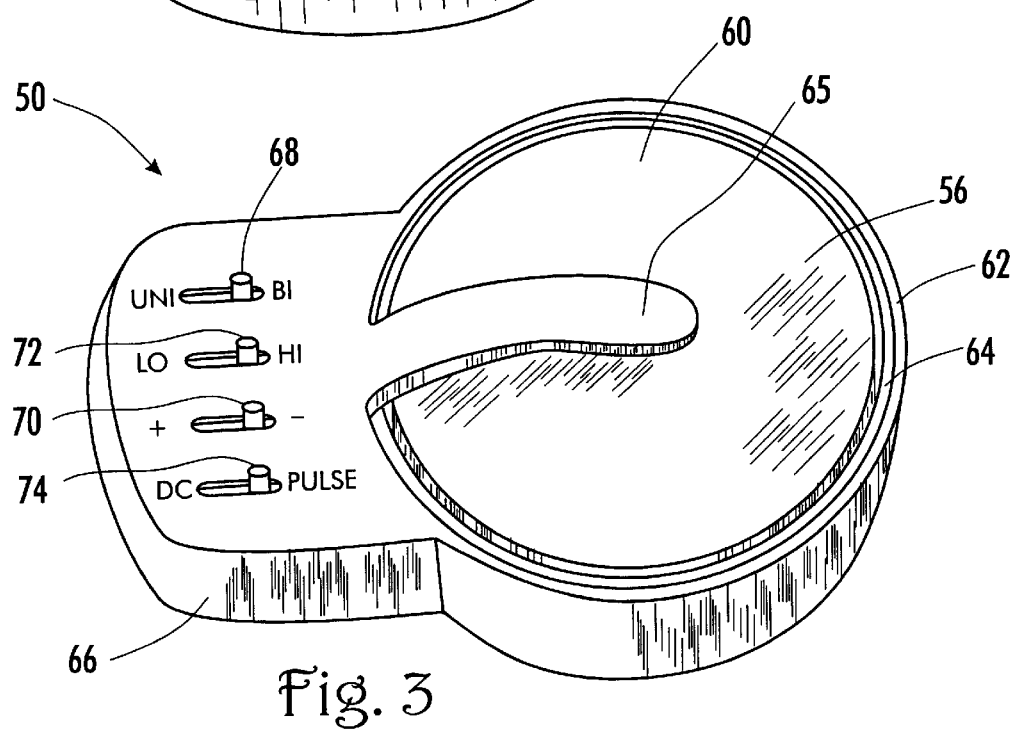
FIG. 3 is an isometric view of the patch disc of FIG. 2, showing the side and top portions of the disc.

According to known practice, the central disc would be the pole changed to the same charge as the pharmaceuticals to be administered, i.e., a positive pharmaceutical is delivered by a positive charge on the disc surface in contact with the gel disc. As shown in FIG. 3, the second pole 60 of battery 56 is electrically connected to the outside ring 62, such as by a contact extension 65 that can be displaced sufficiently to allow the battery to be installed or removed from the disc. The direction of current flow can be changed by such simple measures as reversing the battery 56 on the patch. Thus, in a basic embodiment as illustrated in FIG. 2, the polarity of the patch corresponds to which face of the battery is applied to the top of the patch.

A preferred patch is illustrated in FIG. 3, in which the patch structure 50 includes a processor 66 embedded in the disc structure. The processor may be associated with control circuitry operated by user-selected control switches. The desired control switches cause the processor to vary four operating parameters. A first switch 68 selects whether the current is unipolar or bipolar. A second switch 70 selects the direction of current flow, which is indicated as positive or negative. A third switch 72 selects between a relatively lower micro-amperage current and a higher micro-amperage current. A fourth switch 74 selects whether the circuitry delivers straight DC current or pulsed DC current. These operating parameters are selectively adjusted according to the drugs being administered and other specific factors dependent upon the conditions of administration. A supervising physician best can advise the patient of the preferred settings.

The gel disc is applied to a subject, preferably over a precisely located point identified by use of a point finder, as described. The battery or other current source delivers charged ions of the treating pharmaceuticals from the gel disc and into the subject's skin. Placing the disc over a neurodermal point provides an especially effective location for delivery of the treatment, because electrical resistance is measurably lower at such points. A lower electrical resistance at the neurodermal point will result in greater delivery rate of the pharmaceutical into the subject.

The use of a point finder to locate the nerve or nerves in need of treatment allows the treatment to be delivered precisely, thus producing an effective treatment. Further, this mode of treatment eliminates the prior practice of applying a topical treatment over substantial areas not in need of treatment. Thus, the patient benefits by receiving a quick and effective treatment at the precise location in need of treatment, without application of excessive quantities of the active agents. In these circumstances, side effects of the active agents are minimized.

Although the gel disc preloaded with a composition for treating chronic pain is an especially effective combination for delivery to a precisely located neurodermal point, this method of delivery can be additionally applied with still other pharmaceutical compositions. Accordingly, it is anticipated that this method is useful with any drug or medicament heretofore known or later discovered that is capable of delivery by iontophoresis.

Another preferred composition consists of selected blockers of NMDA receptors and alpha 1 receptors. The active pharmaceutical agents of this composition are dextromethorphan; clonidine, usually administered as clonidine hydrochloride USP; magnesium chloride, available as a hexahydrate USP; and amantadine, available as amantadine hydrochloride.

A mixture of these agents is administered by the previously described methods of FIG. 1. A remarkably effective technique of administration is to locate a suitable administration site by using an electronic point finder. A mixture of these agents, suitable for administration by injection, is placed subcutaneously 26, such as by injection at one or two sites near the preselected point. This simple administration has been found to high effective. The results are comparable to a neural dermal block, which is previously unknown for such topical treatment.

The forgoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be regarded as falling within the scope of the invention.

What is claimed is:

1. A topically effective polypharmaceutical composition consisting essentially of a combination of pharmaceutical agents consisting of an effective dosage of phenoxybenzamine, ketamine, and gabapentin carried in a pluronic lecithin organogel as a topical vehicle, wherein said dosage is a therapeutically effective amount for treating chronic pain by producing a blockade of initiation and propagation of the pain stimulus in the Langerhans and other neuroendocrine vascular structures of the superficial and deep dermis.

2. The composition of claim 1, wherein said pharmaceutical agents consist of phenoxbenzamine, ketamine, and gabapentin in an approximate quantity ratio of 2:5:5.

3. The composition of claim 1, wherein the pharmaceutical agents consist of by volume approximately 2% phenoxbenzamine, 5% ketamine, and 5% gabapentin carried in a topical vehicle.

4. A method of treating pain by producing a producing a blockade of initiation and propagation of the pain stimulus in the Langerhans and other neuroendocrine vascular structures of the superficial and deep dermis of a humnan or animal subject in need of such treatment, comprising:

performing an administration step by topically administering to the subject in need of such treatment a combination of pharmaceutical agents consisting of an effective dosage of phenoxybenzamine, ketamine, and gabapentin carried in a pluronic lecithin organogel as a topical vehicle.

5. The method of claim 4, wherein said administration step is performed by topically applying a spray of the said pharmaceutical agents to the subject's skin.

6. The method of claim 4, wherein said administration step is performed by topically applying a gel cream of the said pharmaceutical agents and topical vehicle to the subject's skin.

7. The method of claim 4, wherein the said pharmaceutical agents consist of phenoxbenzamine, ketamine, and gabapentin in an approximate quantity ratio of 2:5:5.

8. The method of claim 4, wherein the said pharmaceutical agents consist of by volume approximately 2% phenoxbenzamine, 5% ketamine, and 5% gabapentin carried in a topical vehicle.

* * * * *